(12) United States Patent
Neogi et al.

(10) Patent No.: US 6,395,204 B1
(45) Date of Patent: May 28, 2002

(54) PLASTIC WOOD, METHOD OF PROCESSING PLASTIC WOOD, AND RESULTING PRODUCTS

(75) Inventors: Amar N. Neogi, Seattle; Stanley L. Floyd, Enumclaw, both of WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

(21) Appl. No.: 09/494,194

(22) Filed: Jan. 28, 2000

(51) Int. Cl.$^7$ ................................. B27M 1/00

(52) U.S. Cl. ............... 264/37.1; 144/380; 264/122; 264/211.11; 264/211; 264/322; 428/537.1; 800/298

(58) Field of Search ............... 264/119, 109, 264/122, 211, 211.11, 319, 320, 322, 325, 37.1; 428/537.1, 541; 144/380, 381, 271; 800/298

(56) References Cited

U.S. PATENT DOCUMENTS

| | | | |
|---|---|---|---|
| 2,453,679 A | * 11/1948 | Stamm et al. | |
| 3,894,569 A | * 7/1975 | Huttunen | |
| 4,469,156 A | * 9/1984 | Norimoto et al. | |
| 5,343,913 A | * 9/1994 | Tanahashi et al. | |
| 5,451,514 A | 9/1995 | Boudet et al. | 435/172.3 |
| 5,824,842 A | 10/1998 | MacKay et al. | 800/200 |
| 5,850,020 A | 12/1998 | Bloksberg et al. | 800/205 |
| 5,866,791 A | 2/1999 | Holt | 800/205 |

OTHER PUBLICATIONS

Baldwin, S.H. and D. A. I. Goring. The thermoplastic and adhesive behaviour of thermomechanical pulps from steamed wood. *Svensk Papperstidning* 71: 648–650 (1968).

Baucher, Marie et al. Red xylem and higher lignin extractability by down regulating a cinnamyl alcohol dehydrogenase in poplar. *Plant Physiology* 112: 1479–1490 (1996).

Dimmel, D. R., J. MacKay, E. Althen, and C. Parks. Pulping, bleaching, and characterization of CAD–deficient wood. Institute of Paper Science and Technology, Technical Paper Series, No. 787 (1999).

Fergus, B.J. and D. A. I Goring. The location of Guaiacyl and syringyl lignins in birch xylen tissue. *Holzforschung* 24(4): 113–117 (1970).

Halpin, C. et al. Manipulation of lignin quality by down-regulation of cinnamyl alcohol dehydrogenase. *The Plant Journal* 6(3): 339–350 (1994).

Higuchi, T., M. Shimada, F. Nakatsubo, and M. Tanahashi. Differences in biosynthesis of guaiacyl and syringyl lignins in woods. *Wood Science and Technology* 11:153–167 (1977).

MacKay, J. et al. Modified lignin and delignification with a CAD–deficient loblolly pine. *Holzforschung* 53: 403–410 (1999).

Ralph, J. et al. Abnormal lignin in a loblolly pine mutant. *Science* 277: 235–239 (1997).

(List continued on next page.)

Primary Examiner—Mathieu D. Vargot

(57) ABSTRACT

The invention is based on the discovery that the wood of certain trees having genetically modified lignins has plastic properties far greater than that of trees of the general population of the same species. In particular, trees have been found to have significantly increased plasticity in which the lignin is of a less crosslinked or more linear type, of lower molecular weight, of a relatively higher content of lignin precursor monomers or oligomers, or is more readily extractable by the usual methods. Wood from these trees can be readily molded by pressure and heat into two or three dimensional articles. The ability to be molded can be significantly enhanced by the addition of plasticizers.

24 Claims, 3 Drawing Sheets

OTHER PUBLICATIONS

Ralph J. et al. Lignin structure in lignin–biosynthetic–pathway mutants and transgenics; new opportunities for engineering lignin?. 10$^{th}$ International Symposium on Wood and Pulping Chemistry, Yokohama Japan, pp. 138–145 (1999).

Seborg R. M., M. A. Millett, and A. J. Stamm. Heat stabilized compressed wood with "Staypak". Forest products Laboratory, Forest Service, U.S. Department of Agriculture, Publication 1580 (1956).

* cited by examiner

PLASTIC WOOD, METHOD OF PROCESSING PLASTIC WOOD, AND RESULTING PRODUCTS

The present invention is directed to the use of trees having their lignin content and structure modified so that the wood becomes plastic or is more compatible with plasticizing agents. The wood may be molded, extruded, or otherwise treated under heat and pressure to form products conventionally useful as lumber or moldings or it may be formed into many products currently made from molded plastics, composites, or inorganic materials.

BACKGROUND OF THE INVENTION

Over the many millennia of human history and prehistory, trees have been one of natures most valuable and useful products to man. Before modern civilization, the wood that forests provided has been a material for heat, shelter, drugs, flavorings, art, weapons, and even clothing. In more recent times it has additionally had incalculable importance as a source of paper for its myriad uses in communication, personal hygiene care, packaging, and many other products.

Forest types vary over the globe but they may normally be classified as those in which conifers or deciduous trees predominate. The conifers, or so-called softwoods, are the source of most of the world's construction lumber and much of its paper. Deciduous trees, typically known as hardwoods, are much used where appearance is important, as well as for paper products where shorter fibers give advantageous properties. Many deciduous tree species have extremely beautiful wood from the standpoint of color and/or grain pattern. The term "hardwood" is actually a misnomer since actual hardness spans a wide range from extremely soft to very dense. Also, many deciduous trees from tropical or semitropical areas do not seasonally loose their leaves as they do in temperate zones. On the scale of evolutionary development, the deciduous trees have appeared much more recently in geologic time than conifers and are considered to be more advanced. The separation occurs at a high level on the taxonomic scale with the deciduous trees being in the botanical Class Angiospermae while the conifers are encompassed in the Class Gymnospermae. As would be expected, this wide evolutionary separation has resulted in significant differences in morphology and wood chemistry:

If the coniferous woods may be used as a model, they are composed of longitudinal fibers (tracheids) with a much lower number of thin-walled, radially oriented ray parenchyma cells. The tracheids, which are typically 2–5 mm long, are closed at the ends and have a central hollow or lumen extending most of their length. The tracheid walls have multiple layers with a multiplicity of openings (simple or bordered pits) through the walls into the lumen and in communication with similar openings in the adjacent tracheids and parenchyma cells. A layer called the middle lamella is located in the intermediate zone between adjacent tracheids. Structure of the xylem, or woody tissue, of the hardwoods has all of these features with the addition of other functional cells such as large, longitudinal thin-walled vessels.

As is well known, the primary structural and chemical constituent of the tracheids is the polymer cellulose. This occurs in the tracheid walls along with lower molecular weight polymeric sugars (hemicellulose) of somewhat different linkage and composition. In angiosperms the hemicellulose is a mixture of complex hexose and pentose polymers. Gymnosperm hemicellulose has a lower content of the pentose polymers. The tracheid walls are further reinforced with complex heterogeneous aromatic-based polymers referred to as lignin. The lignin is believed to contribute mechanical stiffness and structural integrity to the standing tree. The middle lamella between the tracheids is an amorphous zone composed primarily of hemicellulose and lignin. Middle lamella lignin may or may not be of similar composition to that in the tracheid walls. Fergus and Goring, *Holzfosrchung* 24(4): 113–117 (1970) note that birch lignin in the vessel secondary wall and middle lamella is predominantly composed of one type (guaiacyl) whereas lignin in fiber and ray parenchyma secondary walls is mainly of another type (syringyl). The middle lamella around the fiber and ray cells contained both types.

Lignin is formed during cell development by the sequential expression of several known genes. Lignin formation and composition has been extensively studied and there is an extensive literature on the subject. At some point after the evolutionary separation of the gymnosperms and angiosperms the composition of the lignin followed different paths. Lignin polymers are generally classified into three groups depending on their respective monomer units. The conifers have predominantly crosslinked guaiacyl-type lignins formed as dehydrogenation polymers of coniferyl alcohol. In contrast, hardwood lignins are composed of a roughly equal mixture of guaiacyl and the more linear syringyl-types, the latter being a dehydrogenation polymer of sinapyl alcohol. A third type, guaiacyl-syringyl-p-hydroxyphenyl is found in grasses. These are believed to be the most evolutionarily advanced of the group; e.g., see T. Higuchi et al. *Wood Science Technology* 11: 153–167 (1977). These authors trace the entire biosynthetic pathways of lignin formation in both gymnosperms and angiosperms. Briefly stated, phenylalanine is first deaminated to produce cinammic acid. This is then methylated and hydroxylated to produce the three acids basic to synthesis of the three lignin types. These are then reduced to aldehydes by the enzyme cinnamoyl-CoA reductase (CCR) and finally converted to alcohols (monolignols) by another enzyme cinnamyl alcohol dehydrogenase (CAD). Subsequent polymerization occurs principally at the beta carbon of the propanoid moiety and at $C_5$ of the aromatic ring, although other point of reactivity are also involved.

LIGNIN PERCURSORS

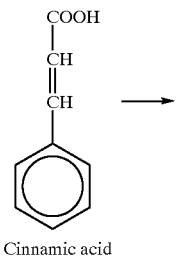

Cinnamic acid

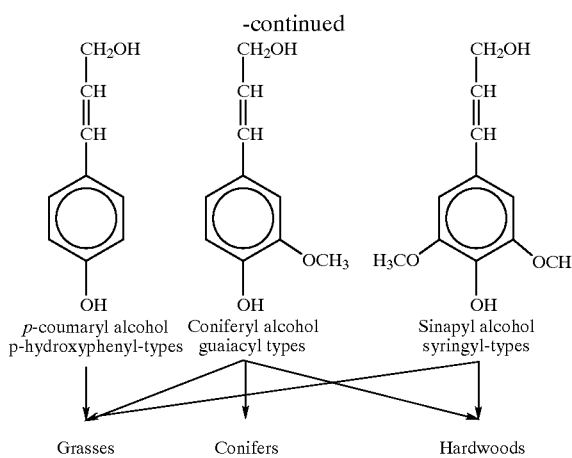

Lignin genesis and chemistry and the history of its investigation is concisely reviewed by E. Adler, *Wood Science and Technology* 11 169–218 (1977). Sarkanen and Ludwig treat the subject in great depth in Lignins. *Occurrence, formation, structure and reactions*, Wiley-Interscience, New York (1971).

The difference in lignin composition is of far more than academic importance. Guaiacyl lignins tend to be far more heavily crosslinked than syringyl types. This affects their relative solubility in the various pulping liquors used for preparation of wood pulps. The syringyl lignin, being a more linear polymer due to one less available crosslinking site, is more readily solubilized and removed by the usual pulping chemicals. All other things being equal, hardwood species are more easily pulped than coniferous species.

Recent research had been directed to finding or creating both coniferous and hardwood trees that have modified lignin more amenable to removal by conventional pulping processes. This research has followed two lines. One is classic genetic selection in which trees having desirable properties are selected and reproduced. The other is genetic transformation in which new genes are introduced into a species by one of the techniques now available.

An example of the genetic selection route is detailed in MacKay et al., U.S. Pat. No. 5,824,842. In a case of serendipitous research, a scientist noted a loblolly pine (*Pinus taeda* L.) which had brownish sap wood in comparison to the usual white wood of the species. Further research revealed that the tree had a mutant gene that failed to produce the enzyme cinnamyl alcohol dehydrogenase (CAD). This enzyme lies on the critical lignin synthesis path for the guaiacyl lignins, acting to convert coniferaldehyde to coniferyl alcohol. The latter of these compounds is the primary lignin precursor in conifers. Although it had been harvested, fortunately the tree was in a research plot and had known parentage with the maternal parent still available as a seed source. Further plantings and crosses originating from the parental seed resulted in trees that were both heterozygous and homozygous in the mutant CAD null allele. Wood from both heterozygous and homozygous trees has been pulped on a micro scale using both the soda and kraft processes; e.g., see MacKay et al., *Holzforschung* 53: 403–410 (1999). The authors concluded that" . . . suppression of CAD in softwood trees may hold promise to produce woods well suited for 'milder' pulping conditions that consume less chemicals . . .". Lignin composition in the CAD deficient trees was significantly modified in comparison to that found in a normal tree; e.g., see Ralph et al. *Science* 277: 235–239 (1997). Guaiacyl lignin was very low and there were increased amount of coniferaldehyde, dihydroconiferyl alcohol, and vanillin and decreased amounts of coniferyl alcohol. The authors particularly note the approximate tenfold increase in dihydroconiferyl alcohol, a monomer not usually associated with the biosynthesis of lignin. This is of considerable practical importance since dihydroconiferyl alcohol lacks the double bond on the propanoid moiety and thus lacks the reaction site at this location. It can form only linear polymers.

Baucher et al., *Plant Physiology* 112: 1479–1490 (1996) report easier lignin extractability in a poplar cross by downregulating CAD. The amount of lignin in juvenile stems was not decreased nor was the syringyl/guaiacyl ratio significantly changed. However, kraft pulping tests indicated greater lignin removal as evidenced by reduced kappa numbers. Similarly, Boudet et al, in U.S. Pat. No. 5,451,514 describe poplar and eucalyptus genes and recombinant DNA containing the genes useful for reducing the level of CAD in a plant. Bloksberg et al. in U.S. Pat. No. 5,850,020 describe genetic modification of lignin in a wide variety of plants including poplar and eucalyptus.

It has long been known that some species of wood can be bent when thoroughly steamed and while still hot. Birch and ash species are exemplary. Bent wood is used extensively in furniture, especially in items such as chair backs. In general, conifers are very difficult to bend without failure on the tension side of the curve. A high wood moisture content is essential and it is well known that moisture serves as a wood plasticizer. Apparently some plastic flow occurs during bending. The U.S. Forest Products Laboratory has developed a heat stabilized compressed wood (Stapak) in which they refer to lignin "flow" under pressure, although no supporting evidence is given; e.g., Seborg et al. Forest Products Laboratory, Forest Service, U.S. Dept. of Agriculture Publication 1580 (1956). Baldwin and Goring, *Svensk Papperstidning* 71(18): 648–650 (1968) describe the thermoplastic and self adhesive behavior of birch, aspen, and black spruce fiber after steam treatment prior and subsequent to mechanical defiberization. They note that the respective softening temperatures for dry hemicellulose and lignin of 160°–200° C. drop markedly when moisture is present.

Bending or compression of wood is primarily a two dimensional deformation. Efforts to mold or otherwise form wood in three dimensions have had very limited success. Yet an analogy might be made between wood and a reinforced plastic. In wood the tracheids form a highly oriented reinforcing fiber and the middle lamella serves as the matrix in which the fibers are embedded. If sufficient flow could be created in the middle lamella it should be possible to form wood into three dimensional and other forms by inexpensive molding rather than by machining as is now required. Since wood is basically a very low cost material, major economic advantages would be realized if it could be substituted in some applications for the much more expensive plastic materials. As one example, the CAD deficient pine noted earlier appears to have a much higher content of lower molecular weight products and is possibly less crosslinked, suggesting that it might be thermoformable. However, efforts at lignin modification to date have been directed to producing more readily pulpable woods. The advantage of the increased plasticity of modified lignin woods has been totally unrecognized to the present time.

SUMMARY OF THE INVENTION

It has been discovered by the present inventors that that the wood of certain trees having naturally or genetically modified lignin has plastic properties, or can be readily plasticized, so that the wood has at least limited flow under appropriate conditions of pressure and temperature. These plastic properties are significantly greater than the wood of similar species trees having normal lignin composition. The wood of trees in which the lignin is relatively uncrosslinked, of lower molecular weight, of a relatively higher content of the monomers and oligomers of lignin percursors, or is readily extractable by the usual methods, has been found to exhibit enhanced plastic behavior. Trees having a relatively high content of syringyl-type lignin and low amounts of guaiacyl lignin, especially in the middle lamella, are among those having this plastic flow. This bias toward modified lignin formation is typical of some plant species having a genetic modification producing a deficiency of the enzyme cinnamyl alcohol dehydrogenase (CAD). It may be assumed that trees having other genetic modifications producing lignins of greater molecular linearity and/or lower molecular weight would have similarly valuable plastic properties. An increased content of these generally lower molecular weight or less crosslinked lignins, especially in the middle lamella region, is conducive to greater plasticity.

The wood of these modified lignin trees having plastic properties can be molded or formed into more complex shapes than has heretofore been possible with normal wood. The terms "molded" or "formed" are used in the context that an original shape or configuration may be shaped into a different permanent and useful configuration by application of pressure at appropriate temperatures. Depending on the nature of the ultimate product, the molded piece may be formed from an original single or unitary piece of wood. Alternatively, it may be formed from a plurality of pieces or particles of wood which are then formed into a unitary piece by application of pressure. True plastic flow has been observed to occur during the molding process. The wood may be comminuted into particles, flakes, strands, or other geometric configurations prior to molding. Additionally, plasticizers or other adjuvants may be added to the modified lignin wood prior to molding. Plasticizers may be those that interact with either lignin or cellulose to improve processability or to modify certain physical or mechanical properties of the wood. For a chemical to function as a plasticizer for a polymer it should have a solubility parameter close to that of the polymer. Chemical agents having solubility parameters close to cellulose, hemicellulose or lignin, most preferably close to all three, are expected to function as effective wood plasticizers. Exemplary effective plasticizers are water, carbon dioxide, sulfur dioxide, dimethylsufloxide (DMSO), dimethylformamide (DMF), ammonia, formaldehyde, urea and ureaformaldehyde condensates, phenols, and phenol-formaldehyde monomers and oligomers. Many chemicals capable of forming hydrogen bonds with lignin are also effective plasticizers. As examples, chemicals with substituents chosen from amines, alcohols including polyols, ketones, carboxylic acids, esters, ethers, amides, isocyanates, nitriles, nitrates, thiols, thio esters, sulfonic acids, sulfonates, sulfoxides, and sulfones can, under certain conditions, serve as wood plasticizers. Many of the above plasticizers can be removed and recovered, if desirable, after formation of the product.

It is within the scope of the invention to include various types of materials which may act as adhesives or as both plasticizers and adhesives among the adjuvants. Adjuvants also include materials that can act as reinforcement or fillers including glass or metal fibers and mineral fillers of which clays, carbonates, and metal oxides would be exemplary.

In one application, the wood is formed into discrete particles that are prepared as a preform or simply placed in a mold and subjected to sufficient pressure at a suitable temperature for an adequate time to prepare a molded product. The wood particles here may be considered analogous to a conventional plastic molding powder. The mold may be a flat platen press or a compression mold. The particles may also be extruded into a linear or planar form. In another application, the lignin modified wood is first formed into elongated strands or splinters. These may be laid up so that the strands are parallel to each other and molded or formed into flat panels or lumber-like products. In this case the fiber orientation is parallel giving the advantage of enhanced strength and stiffness in bending. Sufficient plastic flow occurs so that the particles are permanently joined together, normally without the need for an adhesive.

In a further application, the lignin modified trees may be sawn into conventional lumber. This may then be finished by application of sufficient pressure and heat to produce a smooth surface without significant compression of the interior portion of the lumber piece. In essence, the piece is finished by a process analogous to ironing rather than by planing. One way this is accomplished is by forcing the rough sawn piece through a finishing die. The surfaces may or may not be initially treated with a plasticizer prior to the smoothing treatment. Treatments of this type open the door to significantly less loss into low value or waste products such as chips, planer shavings, or saw dust.

It is within the scope of the invention to selectively densify areas of a wood product to increase strength in zones that will be subjected to the highest stress in use.

Veneers from the lignin modified trees may be pressed into more complex three dimensional shapes, without the usual problem of tearing, than has heretofore been possible.

It is an object of the invention to provide a lignin modified wood having plastic properties for forming into shaped articles.

It is a further object to provide a method for forming wood having plastic properties into shaped molded articles.

It is another object to form lignin modified wood comminuted into particles or strands into unitary articles without the need for adhesives or with only low levels of adhesives.

It is also an object to form wood into predetermined shapes by extrusion.

It is still a further object to provide finished lumber or moldings with lower raw material loss.

These and many other objects will become readily apparent upon reading the following detailed description taken in conjunction with the attached figures.

DETAILED DESCRIPTION OF THE PREFERRED EMBODIMENTS

Figure 1:
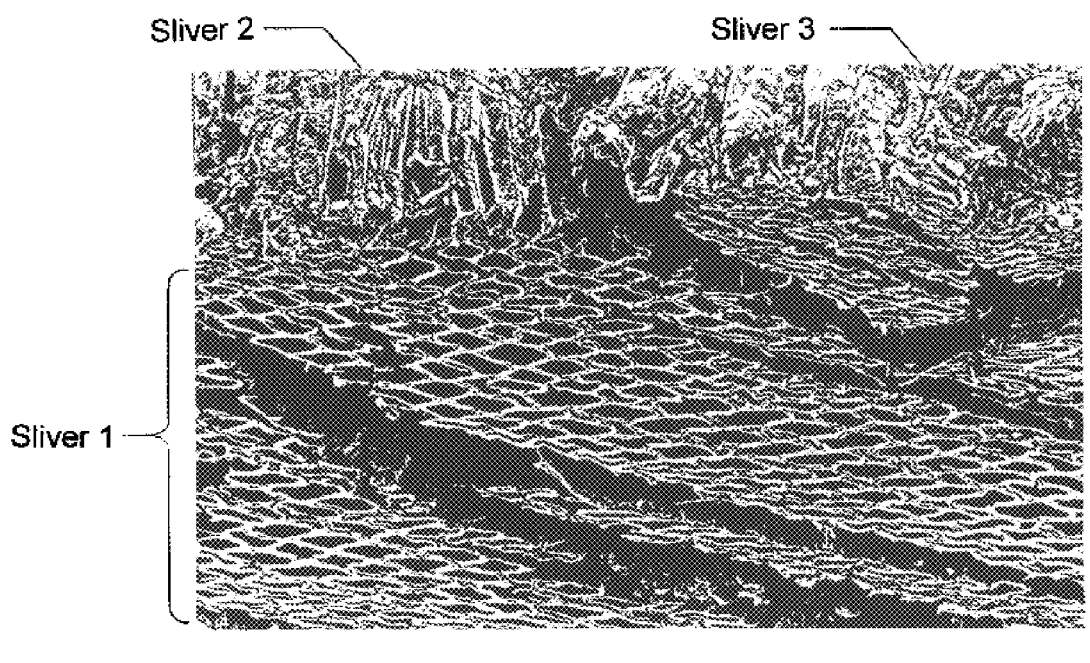
FIG. 1 is a scanning electron micrograph at 200× of a cross section of compressed normal wood chips showing lack of integrity.

Wood is a low cost material with excellent strength and physical properties. It has a major advantage of being a raw material of renewable and sustainable origin. Materials that compete with wood in many applications; e.g., metals, various thermosetting and thermoplastic materials, and inorganic materials such as gypsum or cement products are often of higher raw; material cost but are easier to convert to shaped products. Metals can be cast or formed to products of complex shapes. Plastics are even easier to form into three dimensional products of complex shapes. Thermoset plastics are typically formed by compression or injection molding. However, thermoplastic polymers can be formed into ultimate products by these methods as well as extrusion, rotational molding, casting, calendering, and other methods. Inorganic products such as cement or gypsum are normally cast or extruded as slurries followed by dewatering and curing.

Most of the process to convert wood to an ultimate product involve removal of material to yield a desired shape. The process use sawing, planing, routing ing, sanding, etc. to configure the product to its ultimate form. The large amount of waste materials removed in the shaping processes amount to inefficient use of the raw material. Inexpensive processes used for plastics have not before been practical even though these might be of lower cost and give essentially much more efficient utilization. In most cases, to obtain a smooth and esthetic finished surface on a wood product requires the use of coatings that can add very significantly to the product costs. Prior attempts to smooth wood surfaces by heat and pressure have yielded little success, especially since moisture or high humidity will cause reversion unless the product is treated or impregnated with adhesives or resins.

As was noted before, bending wood is essentially a two dimensional deformation. Reforming wood into three dimensional products has been possible only using thin veneers which are steam treated and molded under heat and pressure. This method introduces significant residual stresses that will be released as dimensional change and deformation when the product is contacted with water or high humidity conditions. Alternatively, the wood may be comminuted into small particles or fibers to which various adhesives are added prior to forming under heat and pressure. The adhesives are essential to ensure structural integrity and stability of the products. Reduction in the required amount of adhesives can sometimes be achieved by refining the wood particles or fibers to expose cellulose surfaces for hydrogen bonding. Again, these bonds are susceptible to loss of strength in moist or high humidity environments.

Many of the difficulties in converting wood to ultimate product configurations can be attributed to the crosslinked structure of the lignin. Modification of lignin to a relatively uncrosslinked or linear state, or to smaller molecules, yields wood that is plastic at elevated temperatures and pressures. Further, the plasticity of wood of this type can be enhanced by the addition of chemicals that act as plasticizers in the same manner that plasticizers are used to enhance certain properties of synthetic thermoplastic polymers. Such modification of lignin in wood is most preferably achieved during growth of the tree and is controlled by the tree's genetic code. As was noted earlier, the genetic code can be modified by the classical method in which trees having desirable properties are selected and further propagated. Alternatively, the newer methods of genetic transformation in which existing genes are altered or foreign genes introduced into normal plants has been extremely effective. The resulting wood can then be converted into products of either simple or complex shapes by many of the same processes used for forming conventional plastic materials. Conversion of comminuted wood into reconstituted two or three dimensional products can be done either with no adhesives at all or with reduced amounts. Plastic flow of the individual particles into a coherent bonded mass occurs in the same manner as the flow of particles of a molding composition into a unitary object. It is also possible to convert wood that has been initially at least partially formed by conventional processing into finished products.

EXAMPLE

Samples of normal and CAD down regulated loblolly pine were obtained as small chips. These were cut to a thickness of about 1.5 mm. Previously dried chips were conditioned 48 hours at 90% RH before testing. Four samples were selected, two with normal lignin and two with modified lignin. One sample of each was pressed between removable cauls for 90 seconds at 93° C. (200° F.). Ram pressure for the normal lignin wood sample was 44,500 N (10,000 lbf). Since the modified lignin sample had twice the surface area of the normal sample the ram force was doubled in order to have the same force per unit area. Before and after pressing dimensions are given in Table 1.

TABLE 1

| Sample | Before Pressing* | | | After Pressing* | | | Area Increase, % | Volume Loss, % |
| --- | --- | --- | --- | --- | --- | --- | --- | --- |
| | Length | Width | Thickness | Length | Width | Thickness | | |
| Normal | 10.9 | 3.4 | 1.44 | 11.5 | 4.8 | 0.65 | 62 | 33 |
| Modified | 13.2 | 5.2 | 1.43 | 14.2 | 6.1 | 0.42 | 27 | 63 |

*All dimensions in mm.

While the normal wood sample showed about twice the increase in surface area in compression, the modified lignin sample showed almost twice as much loss in volume. Grain orientation of the samples was similar so this would not be expected to be a significant factor in the results obtained.

The compression test of Example 1 was repeated with the exception that a single drop of dimethylsulfoxide (DMSO) was placed on each sample and allowed to soak in prior to compression. DMSO is known as an effective wood plasticizer. Excess was removed before the test.

TABLE 2

| Sample | Before Pressing* | | | After Pressing* | | | Area Increase, % | Volume Loss, % |
|---|---|---|---|---|---|---|---|---|
| | Length | Width | Thickness | Length | Width | Thickness | | |
| Normal | 9.8 | 3.4 | 1.45 | Disintegrated | | | — | — |
| Modified | 14.8 | 4.6 | 1.43 | 17.4 | 10.7 | 0.38 | 174 | 17 |

*All dimensions in mm.

In the case of the modified lignin wood treated with DMSO it is notable that there was a significant increase in length (17.6%) compared to only 7.6% for the unplasticized sample. This length increase is considered to be especially significant since it is an indication of the tracheids slipping past each other in a longitudinal direction. Stated otherwise, it is a strong indicator of true plastic flow. Further proof of plastic flow is indicated by the 174% increase in area of the modified lignin wood, as seen in Table 2. By comparison the normal wood sample disintegrated under the conditions used.

Figure 2:
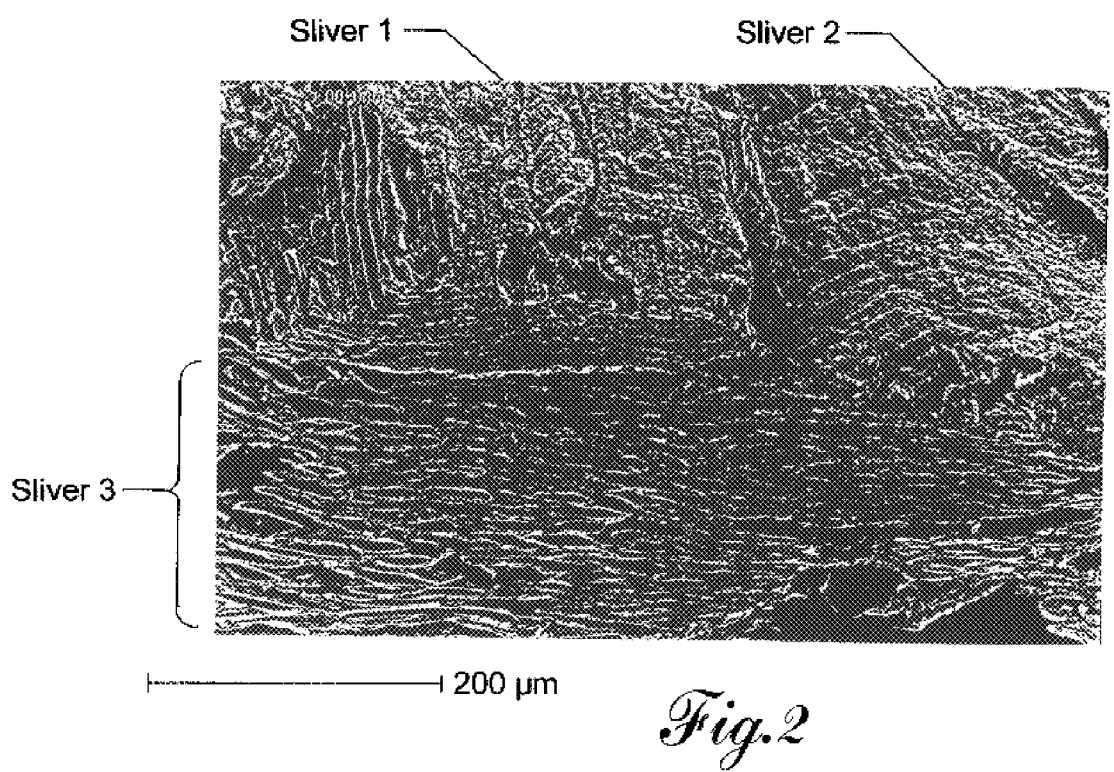
FIG. 2 is a similar electron micrograph at 200× of a cross section of compressed modified lignin wood chips showing good adhesion.
Figure 3:
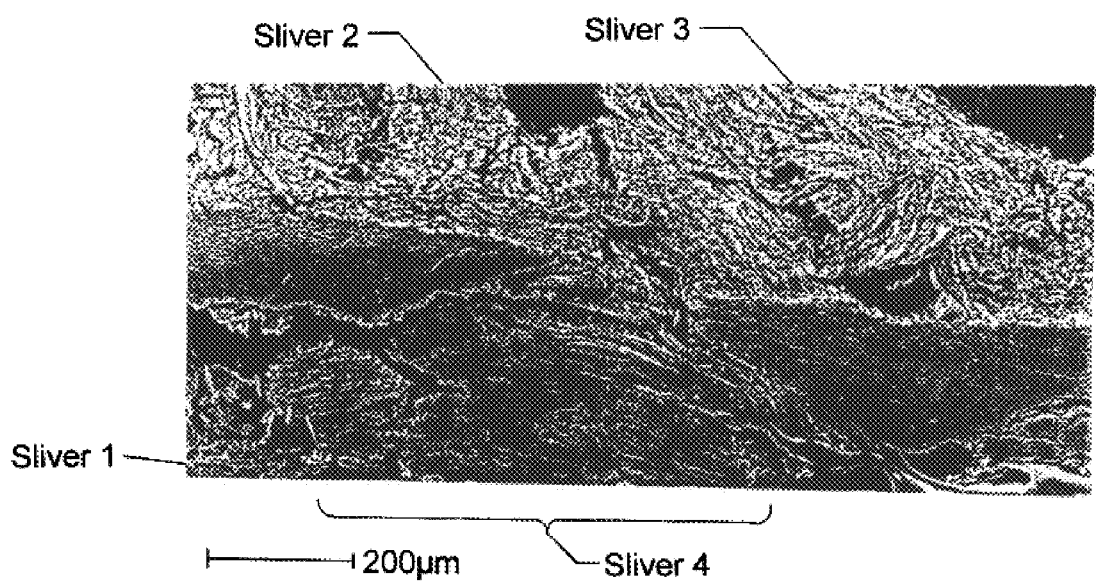
FIG. 3 is a scanning electron micrograph taken at 100× at different location on the compressed sample of FIG. 2.

As another test, slivers of both samples were impregnated with DMSO as above and overlaid one on another on a cool caul. The caul was placed in a heated press at 93° C. for 90 seconds as before. Ram pressure was reduced arbitrarily to 22,250 N (5000 lbf). As seen in FIG. 1, the compressed mat of the normal wood had no integrity and the slivers were readily picked apart. However, the comparison sample with modified lignin wood could not readily be separated into individual slivers and it appeared as if true adhesive bonding had occurred. As seen in FIG. 2, scanning electron micrographs of the cross sectioned mat showed no gaps between adjacent slivers in many locations and boundaries could only be distinguished by fiber orientation, again indicating that true plastic flow had occurred. FIG. 3 is taken at a different location on the modified lignin wood sample shown in FIG. 2. This figure shows the extreme compression of the tracheids resulting from their plasticity.

What is claimed is:

1. A method of making a molded product from wood which comprises:
   selecting wood from a tree genetically modified so that the enzyme cinnamyl alcohol dehydrogenase is suppressed in comparison to trees in the general population of the same species, the modification causing a change in lignin composition so that the selected wood more readily undergoes plastic deformation when subjected to pressure; and
   forming the wood by the application of sufficient pressure at a temperature sufficient to cause plastic flow whereby the wood permanently assumes a preselected configuration.

2. The method of claim 1 in which the lignin is less crosslinked than that found in the general population of the same tree species.

3. The method of claim 1 in which the lignin is of lower average molecular weight than that found in the general population of the same tree species.

4. The method of claim 1 in which the lignin contains a relatively higher content of the monomers and oligomers of lignin percursors than that found in the general population of the same tree species.

5. The method of claim 1 which further comprises selecting the wood from trees having an enhanced ratio of syringyl to guaiacyl types of lignin compared to that found within the general population of the same tree species.

6. The method of claim 1 in which the molded product is formed from a unitary piece of wood prior to the application of pressure.

7. The method of claim 1 in which the molded product is formed from a multiplicity of pieces of wood prior to the application of pressure.

8. The method of claim 7 in which the molded product is formed from wood initially in comminuted form.

9. The method of claims 1, 2, 3, 4, 5, 6, 7, or 8 which includes treating the wood with a plasticizer prior to forming.

10. The method of claim 9 in which the plasticizer is selected from the group consisting of water, dimethylsulfoxide, carbon dioxide, urea, ammonia, and mixtures thereof.

11. The method of claim 8 in which the wood is initially prepared as discrete particles that are formed into a cohesive unitary structure by application of pressure.

12. The method of claim 8 in which the wood is initially prepared as elongated strands which are oriented into a parallel configuration prior to application of pressure whereby the formed article has an essentially parallel fiber orientation.

13. The method of claims 11 or 12 which further includes adding an adjuvant which is an adhesive material.

14. The method of claims 11 or 12 which further includes adding an adjuvant selected from the group consisting of reinforcing materials and fillers.

15. The method of claim 1 which forms the molded product into a panel.

16. The method of claim 1 which forms the molded product into the configuration of lumber.

17. The method of claim 1 which comprises preparing sawn lumber from the trees and finishing the lumber by application of sufficient pressure and heat to produce that a smooth surface without significant compression of the interior portions of the piece.

18. The method of claim 17 which further comprises applying a plasticizer to the surface areas of the sawn lumber prior to application of pressure.

19. The method of claim 17 which comprises forcing the sawn lumber through a heated die.

20. The method of claim 9 in which the plasticizer is removed after forming.

21. The method of claim 20 in which the plasticizer is recovered after removal.

22. A molded product prepared by the method of claims 1, 15, 16, 17, 18, or 19.

23. A molded product prepared by the method of claim 13.

24. A molded product prepared by the method of claim 14.

* * * * *